United States Patent [19]

LeVeen et al.

[11] Patent Number: 4,650,463
[45] Date of Patent: Mar. 17, 1987

[54] PERFORATED TUBING

[76] Inventors: Harry H. LeVeen, 321 Confederate Cir., Charleston, S.C. 29407; Eric G. LeVeen, 358 Summit Ave., Mount Vernon, N.Y. 10552

[21] Appl. No.: 685,539
[22] Filed: Dec. 24, 1984
[51] Int. Cl.⁴ ............................................. A61M 3/00
[52] U.S. Cl. ...................................... 604/43; 604/128
[58] Field of Search ....................... 604/280, 128–129, 604/173, 264, 282, 327, 902, 43–45, 102, 105, 96

[56] References Cited

U.S. PATENT DOCUMENTS

| 1,045,326 | 11/1912 | Ruflin | 604/43 |
| 2,257,369 | 9/1941 | Davis | 604/43 |
| 2,460,473 | 2/1949 | Smith | 604/43 |
| 4,445,897 | 5/1984 | Ekbladh et al. | 604/280 |
| 4,465,481 | 8/1984 | Blake | 604/43 |
| 4,501,580 | 2/1985 | Glassman | 604/43 |

FOREIGN PATENT DOCUMENTS 2248057  5/1975  France ............................ 604/43

Primary Examiner—C. Fred Rosenbaum
Assistant Examiner—Gene B. Kartchner
Attorney, Agent, or Firm—John S. Hale

[57] ABSTRACT

Perforated tubing for surgical drainage applications and the like in which perforations are located in one or more grooves extending lengthwise of the tubing such that the sides of the grooves block access of tissue to the perforations and obturation of the tubing is prevented.

6 Claims, 9 Drawing Figures

PERFORATED TUBING

This invention relates to tubing utilized for medical purposes and in particular provides perforated tubing suitable for surgical drainage and the like.

In the performance of surgery, and in other medical applications such as in the construction of a peritoneo-venous shunt, is frequently necessary to provide for drainage of a body cavity, often with the use of a suction device sometimes by simple application of gravity, and in the case of a peritoneo-venous shunt by utilizing internal body fluid pressure differentials. In common practice perforated tubing is utilized for this purpose, and the drainage device is described as a "sump drain".

A recurring problem in the use of a sump drain is posed by the tendency of tissue to obstruct the drain as fluid movement tends to cause unsecured portions of the tubing to ride against the tissue and then to force the tissue into the perforations.

Commonly, this problem is dealt with by utilizing dual concentric tubing with a perforated outer tube spaced away from a perforated inner tube such that the outer tube holds the tissue away from the inner tube to which the suction is applied (or which is otherwise at a lower pressure) so that the inner tube will not become obstructed and fail to drain. In essence, this arrangement tends to distribute the force of the pressure differential over a wide area and thus to lessen the force applied at any individual perforation.

It is obviously desirable to have the widest possible surface area open to drainage to allow any accumulated fluid to seep through the outer tube where it can be suctioned off, allowed to drain to a collection bottle, or otherwise removed from the sump drain. While it is necessary to expose as large an area as possible to drainage, there are fundamental problems in the use of circular holes or the like for ingress and egress. Once tissue obturates a hole, the tissue can become incarcerated in the hole, since the holes in the perforated tubing are necessarily relatively small and thus form constricting necks. This is particularly true in peritoneal drainage where small outer holes tend to entrap the fatty omentum when suction is applied to the inner tube.

Obviously it would be desirable to provide a perforated tubing for such drainage purposes in which tissue inadvertently trapped can be easily disengaged without the need to exert force which would traumatize the tissue. It is also obviously desirable to provide a sump drain such that the suction apparatus, i.e., tubing, can be constructed relatively simply, preferably as an integral whole, since unitary construction simplifies manufacture and facilitates assembly in the drainage apparatus. Unitary construction is also desirable since there are no joined parts to separate, and the possibility of losing part of the apparatus in the body is thereby minimized.

It is therefore a principal object of the present invention to provide perforated tubing suitable for medical purposes, such as in the construction of a sump drain, in which the possibility of entrapping and incarcerating tissue is minimized. It is a further object of the invention to provide such perforated tubing as a unitary construction which can be formed of extrudable material such as relatively inexpensive plastic materials.

These and other objects of the invention are basically obtained utilizing perforated tubing in which the perforations into the lumen are located in a reentrant wall portion forming a groove and extending lengthwise in the exterior of the tubing. Preferably, a plurality of such grooves are formed in the tubing spaced about the tubing at arcuate intervals and preferably the grooves are of wider cross-section at their bases. In a preferred arrangement the tubing has the shape of a clover leaf in cross-section with an open center (lumen) which communicates with the various grooves, i.e., spaces between the leaves of the clover leaf, through a series of perforations in the bases of the grooves spaced lengthwise along the tubing.

This construction distributes the fluid pressure differential along the entire length of each groove. Since tissue is held away from the central suction area by the side walls of the various grooves, tissue cannot be drawn into the central suction unit (lumen).

For a more complete understanding of the practical application of this invention, reference is made to the appended drawings in which.

Figure 1:
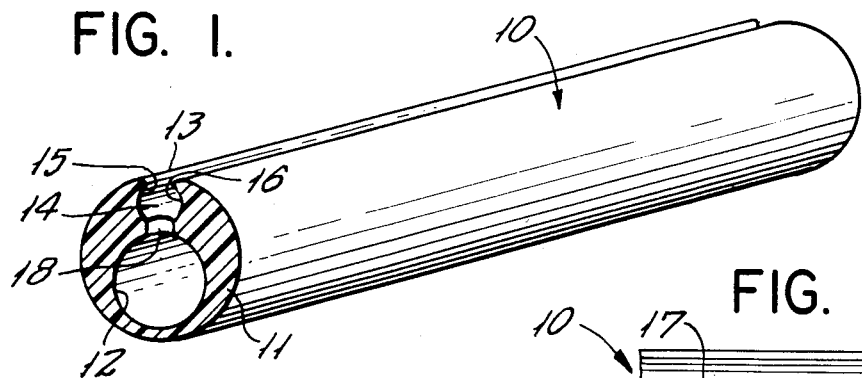
FIG. 1 is a perspective view of a section of perforate tubing in accordance with this invention.
Figure 2:
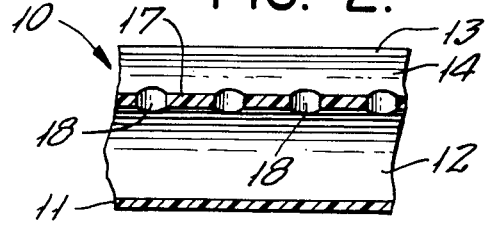
FIG. 2 is a longitudinal section through FIG. 1.

Referring more particularly to FIGS. 1 and 2, the reference numeral 10 indicates a section of perforated tubing in accordance with the present invention formed of extruded elastomer, such as a silicone rubber, which is non-reactive with body fluids. Tubing 10 includes a body portion 11 of overall circular configuration enclosing a passageway 12 forming a lumen extending the length of tubing 10. Passageway 12 is also of generally circular cross-section, but is offset axially, such that body portion 11 is thicker to one side to passageway 12 than the other. In the thick portion of body portion 11, a slot 13 is formed which extends lengthwise of tubing 10 and opens into a groove 14 extending toward passageway 12 formed by juxtaposed side walls 15 and 16. The upper edges of side walls 15 and 16 are spaced apart and parallel, forming slot 13, while the inner ends merge into a bottom 17, such that side walls 15 and 16 are contiguous with bottom 17. Together with bottom 17 side walls 15 and 16 form a generally reentrant wall portion in body 11 which encloses groove 14, except along the exterior of tubing 10 where groove 14 opens through slot 13. As shown best in FIG. 1, groove 14 is interiorly wider in transverse dimension than slot 13.

Bottom 17 of groove 14, which separates groove 14 from lumen 12, is provided with a series of perforations 18, holes which extend through bottom 17 interconnecting groove 14 with lumen 12. Perforations 18 are spaced apart lengthwise of tubing 10.

It will be apparent that the construction can readily be fabricated by conventional extrusion techniques with passageway 12 and groove 14 being formed in body 11 simultaneously with the extrusion. Perforations 18 are added later, and care should be taken to recover the plugs of material which are cut out to form perforations 18. This does not present a problem where the dimensions of perforations 18 are small in relation to the transverse dimensions of passageway 12, if only relatively short lengths of tubing are perforated.

Tubing 10 is utilized as a sump drain in a conventional manner. A suitable length of tubing 10 for forming the sump drain typically is connected to a suction device which communicates with passageway 12 at one end of tubing 10. Fluids to be drained are drawn in through slot 13 and groove 14 and to the interior of passageway 12 through perforations 18 for removal by the suction device. It will be apparent that tissue drawn against slot 13 cannot obturate slot 13, as the tissue generally moves against only a portion of the length of tubing 10 leaving the remainder of slot 13 open to receive fluids. Pressure differentials which would cause incarceration of tissue in slot 13 are not developed because of the distribution of perforations 18 along the length of tubing 10. Fluid flow is readily distributed across the tissue free length of slot 13 without build-up of a pressure differential such as could force the incarceration of tissue in slot 13.

Figure 3:
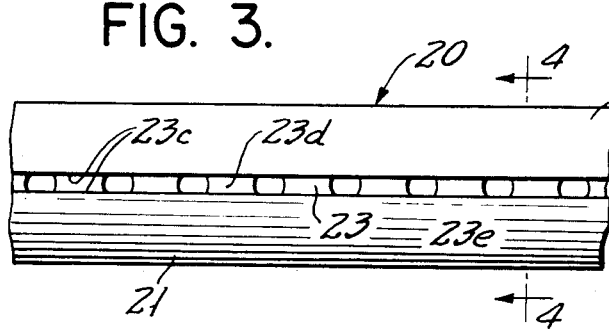
FIG. 3 is an elevation of a length of perforated tubing in accordance with this invention.
Figure 4:
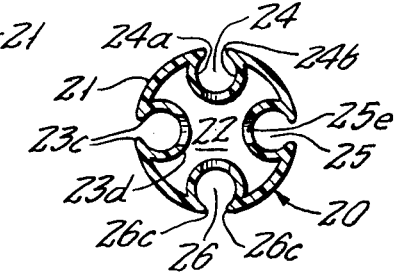
FIG. 4 is a cross-section taken at 4—4 in FIG. 3.

A preferred construction is shown in FIGS. 3 and 4 in which the reference numeral 20 designates a section of perforated tubing in accordance with the present invention having a generally circular overall cross-section formed of a body 21 of relatively thin wall enclosing a central passageway 22. Passageway 22 is of a cloverleaf cross-sectional appearance, as body 21 is provided with four longitudinally extending grooves 23, 24, 25 and 26 which are spaced at ninety degree arcuate intervals about body 21.

Grooves 23, 24, 25 and 26 are identical, except as to location, and are formed by reentrant portions of body 21, each such reentrant portion includes a pair of juxtaposed side walls 23a and 23b, 24a and 24b, 25a and 25b, and 26a and 26b. The outer edges of each associated pair of side walls, such as side walls 23a and 23b, are spaced apart forming a slot 23c in the exterior surface of body 21 which thus forms an opening extending lengthwise of tubing 20 providing access to the associated groove 23. Similarly to the construction shown in FIGS. 1 and 2, the reentrant portion of body 21 forming each groove 23, 24, 25 and 26 is provided with a bottom, such as bottom 23d, which interconnects the inner portions of the associated side walls, such as side walls 23a and 23b with which bottom 23d is contiguous.

As in the arrangement of FIGS. 1 and 2, the grooves of the construction shown in FIGS. 3 and 4 are interiorally of greater transverse dimension than the openings of their associated slots, such as slot 23c in the case of groove 23. This arrangement has the advantage that even in the event portions of tissue might lodge against a slot, such as slot 23c, the spacing in the associated groove 23 internally is large enough to permit flow of fluid about the incarcerated tissue, thus preventing permanent lodgement of the tissue in the slot and facilitating separation of tubing 20 from contact with the tissue.

It will be apparent, particularly observing the transverse shape of tubing 20, that tubing 20 differs substantially from tubing 10 in that body portion 21 of tubing 20 is relatively thin walled and in that passageway 22 extends into the areas between grooves 23, 24, 25 and 26. As pointed out before, the cross-sectional dimensions of passageway 22 have a configuration resembling a clover-leaf.

The construction of tubing 20 is completed by perforations interconnecting various grooves 23, 24, 25 and 26 with passageway 22. These perforations are in the form of a series of holes, such as holes 23e, extending through the bottoms associated with the various grooves, such as bottom 23d. Such holes are preferably of a cross-sectional dimension diameter slightly larger than the opening width of the associated slot, such as slot 23c, and are spaced apart along the bottom, such as bottom 23d, lengthwise of tubing 20 at sufficiently small intervals such that the total cross-sectional area of the holes associated with any given groove, such as holes 23e, have a combined cross-sectional area lengthwise of groove 20 approximating the cross-sectional area of the corresponding slot, such as slot 23c.

Figure 5:
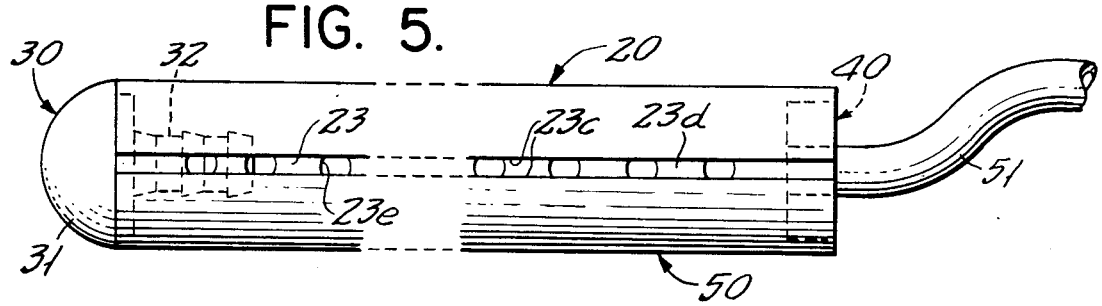
FIG. 5 is an elevation of a peritoneal catheter including a section of perforated tubing in accordance with this invention.

Tubing 20 is generally employed in the same manner as tubing 10 in the construction of sump drains and the like. In the construction of sump drains of permanent nature. FIG. 5 for example, shows a peritoneal catheter 50 utilized as a sump drain in the peritoneum for removal of ascites fluid through a valved peritoneo-venous shunt. A take-off connection through imperforate tubing 51 is provided at one end of a length of perforated tubing 20 The other end of perforated tubing 20 is closed by a plug 30 in order to distribute fluid flow into tubing 20 along its length.

Figure 6:
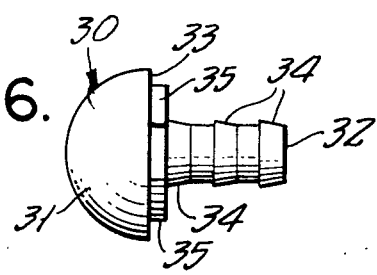
FIG. 6 is an elevation of a plug device for closing an end of the perforated tubing shown in FIG. 5.
Figure 7:
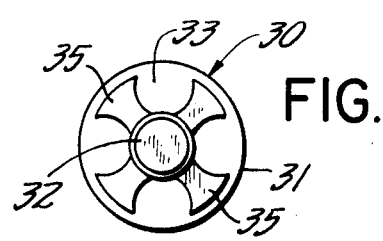
FIG. 7 is an end view of the plug shown in FIG. 6, as seen from the right end.

As shown in FIGS. 6 and 7 plug 30 consists of a cap 31 and a stud 32. Cap 31 is of generally semi-spherical shape having an overall diameter approximating that of tubing 20. Stud 32, which is centrally positioned upstanding on the flat side 33 of cap 31, has a diameter slightly larger than that of a circle tangent to the bottoms 23d, 24d, 25d and 26d of grooves 23, 24, 25 and 26 such that plug 30 can be inserted into an end of tubing 20 with stud 32 pushed into the center of passageway 22. Preferably stud 33 is castellated, as indicated by the reference numeral 34, to facilitate its retention in tubing 20. Preferably plug 30 is further provided with four bosses 35 spaced at ninety degree arcuate intervals about flat side 33 of cap 31 which are shaped to fit into the remaining open portions of passageway 22 formed between adjacent pairs of grooves 23, 24, 25 and 26.

Preferably plug 30 is made of silicone rubber or similar inert material, preferbly the same as tubing 20. Since a peritoneo-venous shunt is a permanent installation, it is preferred that plug 30 be integrally sealed to the end of tubing 20. This can be accomplished using suitable cement or for example, when the materials are thermoplastic, by ultrasonic welding.

Figure 8:
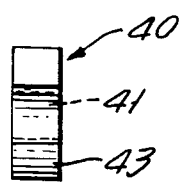
FIG. 8 is a plan view of a connecting device useful in making connection with perforated tubing, such as shown in FIGS. 3 and 4.
Figure 9:
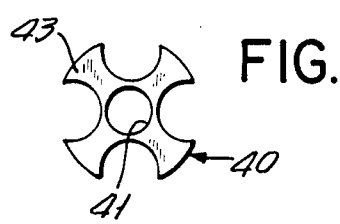
FIG. 9 is a side view of the device shown in FIG. 8.

Connection of tubing 20 in a peritoneo-venous shunt is made to the suction side of the construction through suitable imperforate tubing 51 utilizing a connecting disk 40 shown in FIGS. 8 and 9. Disk 40 has a transverse configuration, as can be seen in FIG. 8, which is identical with the cross-sectional configuration of passageway 22 and is provided with an opening 41 at its center. Disk 40 is sealed into the unplugged end of perforated tubing 20 used as the sump drain to close passageway 22, and the open center of passageway 22 is connected to imperforate tubing 51 leading to the suction side of the shunt. The length of disk 40 should be sufficient to permit adequate sealing of its exterior edges 43 to the inside of body 21. The sealing of edges 43 of disk 40 to body 21 and of the edges of opening 41 to imperforate tubing 51 can be either by use of suitable cement, ultra-sonic welding, or other conventional sealing arrangement.

The assembled plug 30, tubing 20, connector 40 and tubing 51 then form a peritoneal catheter used to drain the peritoneum by connection through suitable valving to the jugular vein, for example.

The choice of materials for construction of perforated tubing in accordance with this invention is dictated by the intended application. As indicated above, materials which are non-reactive with body fluids and tissue, that is, inert materials, are almost necessarily chosen. The designer of a sump drain must also consider the mechanical properties required of the drain. For many applications the material of choice is soft and flexible but should have good cut-through resistance. In some applications, for example, where the tubing must be inserted lengthwise through a body cavity, the tubing should be formed of relatively stiff material.

The mechanical properties of the tubing can, of course, also be influenced by the construction itself. The thickness of the walls of the tubing, the spacing of the perforations between the groove and lumen, and the number of grooves have obvious affect on the flexibility of the tubing.

We claim:

1. A sump drain including a length of perforated tubing, said perforated tubing including a elongated body defining a lumen with a clover leaf cross-section extending lengthwise in said body and open at the ends thereof, groove means located in said body, said groove means defining a groove, a reentrant wall portion having juxtaposed sides defining a slot allowing said groove to communicate with the atmosphere and a bottom portion interconnecting said sides and separating said groove from said lumen, said groove having an interior chamber which is wider in the transverse direction than said slot, and drain means comprising a plurality of spaced perforations extending through said bottom portion allowing communication between said groove and a clover leaf of said lumen, closure means mounted at one end of said body for closing said lumen at said one end, and connector means mounted at the other end of said body adapted to be connected to a suction device.

2. A sump drain according to claim 1 in which said connector means further includes a length of imperforate tubing connected at one end thereof to said lumen at other end of said body.

3. A sump drain according to claim 1 wherein said connector means is take off tubing.

4. A sump drain according to claim 1 wherein said plurality of perforations have a diameter greater than the opening width of the associated slot.

5. A sump drain according to claim 1 wherein said plurality of perforations have a total cross-sectional area which is approximately equal to the cross-sectional area of the associated slot.

6. A sump drain comprising a length of perforated tubing, said perforated tubing including an elongated body defining a throughgoing lumen with a four leaf clover cross-section extending lengthwise through said body, a plurality of opposing grooves defined by said body extending lengthwise on said body at spaced intervals around said body, each groove being defined by wall portions having juxtaposed sides defining a slot allowing said groove to communicate with the atmosphere and a bottom portion interconnecting said sides and separating said groove from said lumen, said groove having an interior chamber which is wider in the transverse direction than said slot and drainage means comprising a plurality of spaced perforations extending through said bottom portion and providing communication between said groove and said lumen, said perforations having a total cross-sectional area which is at least approximate to the cross-sectional area of the associated slot and are axially aligned with the perforations of an opposing groove, closure means mounted at one end of said body closing said lumen at one end and connector means mounted at the other end of said body for connection to a suction means.

* * * * *